United States Patent [19]

Le Tourneau et al.

[11] Patent Number: 4,734,431

[45] Date of Patent: Mar. 29, 1988

[54] THIOPYRANODIPYRAZOLES AND THEIR USE AS BRONCHODILATORS

[75] Inventors: Michael E. Le Tourneau; Norton P. Peet, both of Indianapolis, Ind.

[73] Assignee: Merrell Dow Pharmaceuticals Inc., Cincinnati, Ohio

[21] Appl. No.: 7,308

[22] Filed: Jan. 27, 1987

[51] Int. Cl.[4] .................. A61K 31/415; C07D 231/00
[52] U.S. Cl. .................................... 514/407; 548/370
[58] Field of Search ......................... 548/370; 514/407

[56] References Cited

U.S. PATENT DOCUMENTS 3,158,619  11/1964  Wagner ............................. 548/370
4,042,373  8/1977  Moje ................................. 548/370

Primary Examiner—Henry R. Jiles
Assistant Examiner—Kurt G. Briscoe
Attorney, Agent, or Firm—John J. Kolano

[57] ABSTRACT

The present invention is directed to a group of compounds which are variously methylated thiopyranodipyrazoles and to the S-oxides and S-dioxides of such compounds. The compounds are useful as bronchodilators and are prepared by the reaction of appropriately 5-substituted thiopyrano[3,4-c]pyrazol-4-(1H)-one with a hydrazine.

4 Claims, No Drawings

THIOPYRANODIPYRAZOLES AND THEIR USE AS BRONCHODILATORS

The present invention is directed to a group of compounds which are methylated thiopyranodipyrazoles and S-oxides thereof. More particularly, the present invention is directed to a group of compounds having the formula:

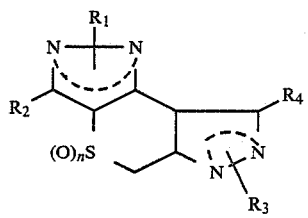

wherein $R_1$, $R_2$, $R_3$ and $R_4$ are each independently hydrogen or methyl with $R_1$ and $R_3$ being positioned on one of the nitrogens in their respective rings with the other nitrogen then being doubly bonded to the adjacent carbon; the dotted lines indicate the presence of two conjugated double bonds with the specific position of the double bonds being determined by the position of the $R_1$ or $R_3$ substituents; and n is 0, 1 or 2. The present invention further encompasses the pharmaceutically acceptable acid addition salts of the aforesaid compounds.

Acid addition salts of the aforesaid compounds with pharmaceutically acceptable acids are equivalent to the above amines for the purposes of this invention. Illustrative of such salts are the salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicyclic, 4-aminosalicyclic, 2-phenoxybenzoic, 2-acetoxybenzoic, mandelic and like acids; and with organic sulfonic acids such as methanesulfonic acid and p-toluenesulfonic acid.

Preferred embodiments of the present invention are those compounds wherein n is 0.

The compounds of the present invention are prepared by the reaction of a hydrazine of the formula

wherein $R_1$ is hydrogen or methyl, with a 1,3-diketone of the formula

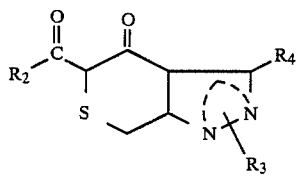

wherein $R_2$, $R_3$ and $R_4$ are each independently hydrogen or methyl. The reaction is carried out with heating in an inert solvent such as an alcohol, with methanol being preferred. The product obtained, in which n is 0, is optionally oxidized with a peroxybenzoic acid to give those compounds in which n is 1 or 2. When $R_1$ or $R_3$ is hydrogen, the product is further optionally treated with sodium hydride and methyl iodide in an inert solvent such as dimethylformamide to give the corresponding compounds wherein $R_1$ or $R_3$ is methyl. When the process gives a mixture of products with substitution on either nitrogen in the rings in question, the resultant mixture is separated by chromatography.

The 1,3-diketone used as the starting material above can be prepared from a thiopyranopyrazolone of the formula

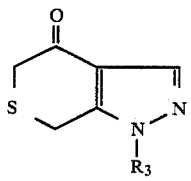

This ketone is reacted with a strong base and an appropriate carbonyl compound to give the diketone. More specifically, sodium hydride and ethyl formate or a combination of diisopropylamine, n-butyllithium and acetyl chloride are used.

The substituted dipyrazole compounds as described herein are bronchodilators and are thus useful in the treatment of bronchial disorders such as bronchial asthma. The present invention is further directed to a method of effecting bronchodilation.

In practicing the method of this invention, an effective bronchodilating amount of 1 or more substituted dipyrazoles of this invention is administered internally to a mammal in need thereof by a route effective to bring the compound into contact with the bronchial and tracheal tissues of the mammal. Administration can be carried out either by a parenteral route, such as by intravenous, intraperitoneal or intramuscular injection, or by introduction into the gastrointestinal tract via oral or rectal administration, for example, in order to bring about such contact via the blood stream, or by intratracheal administration, by inhalation of a solution in the form of a spray, for example.

The effective bronchodilating amount of the compound, that is, the amount sufficient to inhibit or alleviate bronchial spasm, depends on various factors such as the size, type and age of the animal to be treated, the particular compound or pharmacologically-acceptable salt employed, the route and frequency of administration, the severity of any spasm and the causative agent involved, and the time of administration. In particular cases, the dosage to be administered can be ascertained by conventional range finding techniques, for example, by observing the bronchodilator activity produced at different dosage rates. More specifically, the compounds can be administered at dosage rates ranging from about 0.2 to about 100 milligrams of substituted dipyrazole compound per kilogram of animal body weight with other ranges being from about 0.5 to about 20 or from 1 to about 5 milligrams per kilogram. It is generally desirable to administer individual dosages at the lowest amount which provides the desired protection from bronchial spasm consonant with a convenient dosing schedule. Dosage units adaptable to oral administration such as tablets, capsules, lozenges, elixirs, syrups and the like are generally preferred and the active compound can be formulated in conventional time release capsule or tablet formulations although injectable compositions or sprays and aerosols for inhalation are preferred when rapid action is desired. In an example of an individual dosage unit, a tablet would contain 200 mg of active ingredient and would be administered 1 to 6 times daily or, preferably, 2 to 4 times daily.

In practicing the method of the invention, the active ingredient is preferably incorporated in a composition comprising a pharmaceutical carrier and from about 5 to about 90 percent by weight of the substituted dipyrazole compound or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, lozenges, troches, suppositories, elixirs, syrups, emulsions, dispersions, wettable and effervescent powders, sterile injectable compositions and solutions for sprays, and can contain suitable excipients known to be useful in the preparation of the particular type of compositions desired. Suitable pharmaceutical carriers and formulation techniques are found in standard texts, such as *Remington's Pharmaceutical Sciences*, Mack Publishing Company, Easton, Pa.

In evaluating bronchodilator activity, test compounds were administered to guinea pigs by intraperitoneal injection or orally and the guinea pigs were challenged by exposure to a histamine aerosol at periods ranging from 15 minutes to 4 hours later. Untreated animals collapsed when exposed to the histamine aerosol. In the operations, the animals were observed and collapse times were recorded. The collapse times observed were then compared statistically with control animals treated with water alone with the control group usually being a long-term cumulative control. The actual dose of test compound administered was generally 30% of the $LD_{50}$ administered intraperitoneally. Some specific doses of compounds used in the testing are as follows:
5,6-Dihydro-6-methyl-1H-thiopyrano[3,2-c:5,4-c']dipyrazole; 110 mg/kg.
5,6-Dihydro-6-methyl-1H-thiopyrano[3,2-c:5,4-c']dipyrazole 4-oxide; 163 mg/kg.
5,6-Dihydro-6-methyl-1H-thiopyrano[3,2-c:5,4-c']dipyrazole 4,4-dioxide; 163 mg/kg.

When tested by the above procedure, the compounds of the present invention were found to produce a bronchodilating effect.

The following examples are presented to illustrate the present invention but they should not be construed as limiting it in any way.

EXAMPLE 1

A mixture of sodium hydride (8.8 g of a 60% suspension in mineral oil), 8.9 ml of ethyl formate, 3 drops of ethanol and 400 ml of tetrahydrofuran was prepared and stirred as a solution of 18.5 g of 1-methyl-5,7-dihydrothiopyrano[3,4-c]pyrazol-4(1H)-one in 100 ml of tetrahydrofuran was added dropwise. The mixture was heated at reflux for 4 hours and cooled. It was diluted with 200 ml of water and 100 ml of ethyl ether and stirred briefly. The aqueous layer was separated and washed with dichloromethane and then acidified with aqueous hydrochloric acid. The solid which formed was separated by filtration and dried to give an off-white solid which was 1,4,5,7-tetrahydro-1-methyl-4-oxothiopyrano[3,4-c]pyrazole-5-carboxaldehyde melting at about 158°–160° C. An analytical sample, melting at about 158°–159° C., was obtained by recrystallization from ether and dichloromethane.

If the above procedure is repeated using 1,3-dimethyl-5,7-dihydrothiopyrano[3,4-c]pyrazol-4(1H)-one, the product obtained is 1,4,5,7-tetrahydro-1,3-dimethyl-4-oxothiopyrano[3,4-c]pyrazole-5-carboxaldehyde. [The necessary starting material is obtained by following the procedures described by G. Menozzi et al., *J. Het. Chem.*, 21, 1437 (1984) and H. Smith, *J. Chem. Soc.*, 803 (1953).]

If the procedure of the first paragraph is repeated using diisopropylamine, n-butyllithium in hexane, and acetyl chloride in place of the sodium hydride and ethyl formate, the product obtained is 5-acetyl-5,7-dihydro-1-methylthiopyrano[3,4-c]pyrazol-4(1H)-one.

EXAMPLE 2

Hydrazine (3.5 ml) was added dropwise to a solution of 1,4,5,7-tetrahydro-1-methyl-4-oxothiopyrano[3,4-c]pyrazole-5-carboxaldehyde in 250 ml of methanol. The resulting solution was heated at reflux for 45 minutes and then stirred at room temperature for 16 hours. The solvent was removed under reduced pressure and the residue was triturated with ether to give an orange solid (93% yield) melting at about 196°–200° C. Recrystallization of this solid from a mixture of ethanol and water gave 5,6-dihydro-6-methyl-1H-thiopyrano[3,2-c:5,4-c']dipyrazole melting at about 224°–226° C.

If the above procedure is repeated using hydrazine and the appropriate diketones, there is obtained 5,6-dihydro-6,8-dimethyl-1H-thiopyrano[3,2-c:5,4-c']dipyrazole and 5,6-dihydro-3,6-dimethyl-1H-thiopyrano[3,2-c:5,4-c']dipyrazole.

If the procedure of the first paragraph is repeated using the same carboxaldehyde but using methyl hydrazine in place of hydrazine, the product obtained is a mixture of isomers. These are separated by chromatography to give 5,6-dihydro-1,6-dimethyl-1H-thiopyrano[3,2-c:5,4-c']dipyrazole and 5,6-dihydro-2,6-dimethyl-2H-thiopyrano[3,2-c:5,4-c']dipyrazole.

EXAMPLE 3

A solution of 1.06 g of 3-chloroperoxybenzoic acid in 30 ml of tetrahydrofuran was added dropwise to a solution of 5,6-dihydro-6-methyl-1H-thiopyrano[3,2-c:5,4-c']dipyrazole in 20 ml of tetrahydrofuran maintained at −15° C. The mixture was stirred at −15° C. for 3 hours and the solid which formed was separately by filtration and dried to give yellow powdery crystals (93% yield). Recrystallization of this solid from ethanol gave 5,6-dihydro-6-methyl-1H-thiopyrano[3,2-c:5,4-c']dipyrazole 4-oxide melting at greater than 270° C.

EXAMPLE 4

A solution of 7.9 g of 85% 3-chloroperoxybenzoic acid in 50 ml of dichloromethane was added dropwise to an ice-cold solution of 5,6-dihydro-6-methyl-1H-thiopyrano[3,2-c:5,4-c']dipyrazole in 100 ml of dichloromethane. The mixture was stirred at room temperature for 24 hours and the solvent was removed under reduced pressure. Trituration of the residue with tetrahydrofuran gave an orange-yellow solid (67% yield) melting at about 238° C. with decomposition. Recrystallization of this solid from methanol gave 5,6-dihydro-6-methyl-1H-thiopyrano[3,2-c:5,4-c']dipyrazole 4,4-dioxide melting at greater than 270° C.

What is claimed is:

1. A compound of the formula

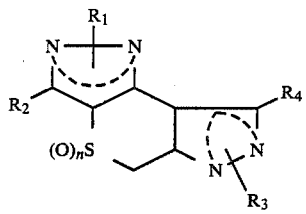

wherein $R_1$, $R_2$, $R_3$ and $R_4$ are each independently hydrogen or methyl with $R_1$ and $R_3$ being positioned on one of the nitrogens in their respective rings with the other nitrogen then being doubly bonded to the adjacent carbon; the dotted lines indicate the presence of two conjugated double bonds with the specific position of the double bonds being determined by the position of the $R_1$ and $R_3$ substituents; and n is 0, 1 or 2.

2. A compound according to claim 1 which has the formula

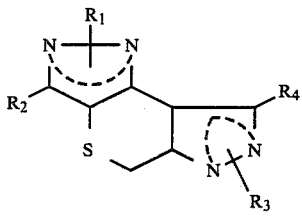

wherein $R_1$, $R_2$, $R_3$ and $R_4$ are each independently hydrogen or methyl with $R_1$ and $R_3$ being positioned on one of the nitrogens in their respective rings with the other nitrogen then being doubly bonded to the adjacent carbon; the dotted lines indicate the presence of two conjugated double bonds with the specific position of the double bonds being determined by the position of the $R_1$ and $R_3$ substituents.

3. A compound according to claim 1 which is 5,6-dihydro-6-methyl-1H-thiopyrano[3,2-c:5,4-c']dipyrazole.

4. A method for alleviating bronchial spasm in mammals which comprises administering to a mammal in need thereof a bronchodilating amount of a compound of the formula

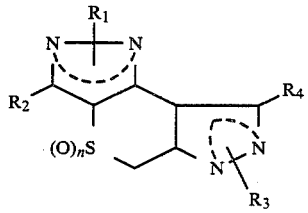

wherein $R_1$, $R_2$, $R_3$ and $R_4$ are independently hydrogen or methyl with $R_1$ and $R_3$ being positioned on one of the nitrogens in their respective rings with the other nitrogen then being doubly bonded to the adjacent carbon; the dotted lines indicate the presence of two conjugated double bonds with the specific position of the double bonds being determined by the position of the $R_1$ and $R_3$ substituents; and n is 0, 1 or 2.

* * * * *

UNITED STATES PATENT AND TRADEMARK OFFICE
CERTIFICATE OF CORRECTION

PATENT NO. : 4,734,431

DATED : March 29, 1988

INVENTOR(S) : Michael E. LeTourneau and Norton P. Peet

It is certified that error appears in the above-identified patent and that said Letters Patent are hereby corrected as shown below:

```
Column 4, line 50, "was separately by" should read
-- was separated by --.

Column 6, line 26, "are independently" should read
-- are each independently --.
```

Signed and Sealed this

Fourteenth Day of February, 1989

*Attest:*

DONALD J. QUIGG

*Attesting Officer*   *Commissioner of Patents and Trademarks*